(12) United States Patent
Witte et al.

(10) Patent No.: US 8,858,652 B2
(45) Date of Patent: Oct. 14, 2014

(54) CONDITIONING DYEING AGENT FOR KERATINOUS FIBERS

(71) Applicant: Henkel AG & Co. KGaA, Dusseldorf (DE)

(72) Inventors: Christiane Witte, Hetlingen (DE); Stephan Schwartz, Wedel (DE)

(73) Assignee: Henkel AG & Co. KGaA, Duesselford (DE)

( * ) Notice: Subject to any disclaimer, the term of this patent is extended or adjusted under 35 U.S.C. 154(b) by 0 days.

(21) Appl. No.: 14/213,364

(22) Filed: Mar. 14, 2014

(65) Prior Publication Data

US 2014/0196222 A1    Jul. 17, 2014

Related U.S. Application Data

(63) Continuation of application No. PCT/EP2012/068244, filed on Sep. 17, 2012.

(30) Foreign Application Priority Data

Sep. 20, 2011    (DE) .......................... 10 2011 083 021

(51) Int. Cl.
| | | |
|---|---|---|
| *A61Q 5/10* | (2006.01) | |
| *A61K 8/81* | (2006.01) | |
| *A61K 8/60* | (2006.01) | |
| *A61K 8/37* | (2006.01) | |
| *A61K 8/42* | (2006.01) | |
| *A61K 8/40* | (2006.01) | |

(52) U.S. Cl.
CPC ................ *A61K 8/37* (2013.01); *A61K 8/8152* (2013.01); *A61K 8/60* (2013.01); *A61K 8/42* (2013.01); *A61K 8/8158* (2013.01); *A61K 8/40* (2013.01); *A61Q 5/10* (2013.01)
USPC ................ 8/405; 8/406; 8/407; 8/552; 8/554; 8/580; 8/582; 8/594

(58) Field of Classification Search
USPC ............ 8/405, 406, 407, 552, 554, 580, 582, 8/594
See application file for complete search history.

(56) References Cited

U.S. PATENT DOCUMENTS 7,294,153 B2 *  11/2007  Kleen et al. ...................... 8/405

FOREIGN PATENT DOCUMENTS

| | | |
|---|---|---|
| DE | 10163860 | 7/2003 |
| EP | 1555010 | 7/2005 |
| FR | 2849774 | 7/2004 |
| WO | 9747282 | 12/1997 |
| WO | 0147480 | 7/2001 |
| WO | 2005082321 | 9/2005 |

OTHER PUBLICATIONS

STIC Search Report dated May 30, 2014.*
Jorge Kahre, APG: Innovative Surfactants Made from Sugar and Fat, Skin Care Forum, Jul. 1, 1995, pp. 1-3, www.skin-care-forum.basf.com/docs/archivausgaben-1-20/scf12_gb_may1995.pdf.

* cited by examiner

*Primary Examiner* — Eisa Elhilo
(74) *Attorney, Agent, or Firm* — Steven L. Nichols; Van Cott, Bagley, Cornwall & McCarthy P.C.

(57) ABSTRACT

The specification describes an agent for coloring keratinic fibers. The agent includes, in a cosmetically acceptable carrier, at least one oxidation dye precursor, a precursor of a nature-analogous dye, a substantive dye, or combinations thereof. The agent also includes a carrier base combination. The carrier base combination includes at least one fatty substance of formula (I), in which R and R' in each case mutually independently denote a saturated or unsaturated $C_6$-$C_{22}$ alkyl chain; at least one nonionic surfactant of formula (II),R1-O-$[G]_p$(II) in which R1 denotes a saturated or unsaturated $C_6$-$C_{22}$ alkyl chain, G denotes a sugar residue with 5 or 6 carbon atoms and p denotes a number from 1 to 10; and at least one cationic polymer, at least one amphoteric polymer, or combinations thereof.

15 Claims, No Drawings

CONDITIONING DYEING AGENT FOR KERATINOUS FIBERS

RELATED APPLICATIONS

The present specification is a U.S. continuation patent application under 35 U.S.C. 111(a) and claims the right of priority under 35 U.S.C. 365 to international patent Application No. PCT/EP2012/068244, filed Sep. 17, 2012, entitled "CONDITIONING DYEING AGENT FOR KERATINOUS FIBRES" which claims benefit of German application No.: 102011083021.9, filed Sep. 20, 2011, these applications are herein incorporated by reference in their entirety.

FIELD OF THE INVENTION

The present invention generally relates to coloring agents for keratin-containing fibers for high intensity, long-lasting coloring results combined with an improved conditioning state of the keratinic fibers.

BACKGROUND OF THE INVENTION

Consumers make use of color-modifying agents to obtain fashionable coloring of hair or to conceal grayed or even white hair with fashionable or natural color shades. Apart from the desired color modification, these agents should cause the least possible damage to the hair, indeed they should preferably even have additional conditioning properties and make the hair visually attractive. Depending on the requirements placed on the color modification, many coloring systems may provide coloring cosmetics, in particular for the skin or keratin-containing fibers such as for example human hair.

"Oxidation coloring agents", may refer to agents used for permanent, high intensity dyed colors with appropriate fastness characteristics. Such coloring agents may contain oxidation dye precursors which, under the influence of oxidizing agents or atmospheric oxygen, react with one another to form the actual dyes. Oxidation coloring agents may be distinguished by excellent, long-lasting coloring results. Coloring agents or tints which contain "substantive" dyes as the coloring component may be used for temporary coloring. These "substantive" dye molecules may key directly to the substrate and may not need an oxidative process to develop the color. Finally, coloring systems based on precursors of nature-analogous dyes are used, in which the precursor compounds, predominantly under the influence of atmospheric oxygen, react with one another and, in so doing, form colored macromolecules similar in structure to natural melanin dyes. However, after color modification, in particular after an oxidative color modification, the hair is frequently left in a state which is rather unattractive in tactile and visual terms.

Accordingly, the present specification reduces the above-stated disadvantages of conventional commercial hair coloring agents. The color modifying agents of the present specification as far as possible reduce fiber structure damage, impart elevated resilience and silkiness, and in particular impart improved combability to the hair. This, however, is not achieved at the expense of reduced color modification performance of the agents. In particular, the coloring agents achieve glossy, bright, long-lasting and uniform coloring results.

Furthermore, other desirable features and characteristics of the agents described in the present specification will become apparent from the subsequent detailed description of the invention and the appended claims, taken in conjunction with the accompanying drawings and this background of the invention.

BRIEF SUMMARY OF THE INVENTION

An agent for coloring keratinic fibers, containing, in a cosmetically acceptable carrier, at least one oxidation dye precursor, a precursor of a nature-analogous dye, a precursor of a substantive dye, or combinations thereof. The agent also contains a carrier base combination. The carrier base combination includes at least one fatty substance of formula (I),

in which R and R' in each case mutually independently denote a saturated or unsaturated $C_6$-$C_{22}$ alkyl chain. The carrier base combination also includes at least one nonionic surfactant of formula (II),

in which R1 denotes a saturated or unsaturated $C_6$-$C_{22}$ alkyl chain, G denotes a sugar residue with 5 or 6 carbon atoms and p denotes a number from 1 to 10. The carrier base combination also includes at least one cationic polymer, amphoteric polymer, or combinations thereof.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In some examples, a specific combination of ingredients in the carrier base of coloring agents for keratinic fibers in particular has a positive influence on the conditioning performance and level of damage to fibers and on the coloring results. This ensures not only an improved conditioning state but also coloring results which are equal or even superior to those of conventional products.

The present specification firstly provides an agent for coloring keratinic fibers, containing in a cosmetically acceptable carrier at least one oxidation dye precursor, a precursor of a nature-analogous dye, a substantive dye or combinations thereof. The agent also contains a carrier base combination. The carrier base combination first includes at least one fatty substance of formula (I),

in which R and R' in each case mutually independently denote a saturated or unsaturated $C_6$-$C_{22}$ alkyl chain. The carrier base combination also includes
at least one nonionic surfactant of formula (II), R1-O-[G]$_p$                                    (II), in which R1 denotes a saturated or unsaturated $C_6$-$C_{22}$ alkyl chain, G denotes a sugar residue with 5 or 6 carbon atoms and p denotes a number from 1 to 10. The carrier base combination also includes at least one cationic polymer, amphoteric polymer, or combinations thereof.

As used in the present specification and in the appended claims, the term "keratinic fibers" may refer to furs, wool, feathers and in particular human hair. Although the agents according to the present specification may be primarily suitable for coloring keratin fibers, they may also be used in other fields.

The preparations of the present specification may contain the active substances in a cosmetically acceptable carrier. Said cosmetic carrier may be aqueous, alcoholic or aqueous-alcoholic. As used in the present specification and in the appended claims, an aqueous-alcoholic solution may refer to a hydrous solution containing 3 to 70 wt. % of a $C_1$-$C_4$ alcohol, in particular ethanol or isopropanol, relative to the total weight of the mixture. The agents may additionally contain further organic solvents, such as for example 4-methoxybutanol, ethyl diglycol, 1,2-propylene glycol, n-propanol, n-butanol, n-butylene glycol, glycerol, diethylene glycol monoethyl ether and diethylene glycol mono-n-butyl ether. Any water-soluble organic solvent is preferred for this purpose. An aqueous carrier may contain at least 30 wt. %, in particular at least 50 wt. % water, relative to the total weight of the mixture. Carriers suitable for the purpose of hair coloring are for example creams, emulsions, gels or also surfactant-containing foaming solutions, such as for example shampoos, foam aerosols or other preparations which are suitable for use on the hair. Preferred carriers include emulsions and gels, wherein emulsions are particularly preferred.

The agent may contain at least one oxidation dye precursor and/or a precursor of a nature-analogous dye and/or a substantive dye as an essential ingredient.

In a preferred example, the agent may contain at least one oxidation dye precursor as color-imparting component.

The coloring preparations may contain at least one developer component and optionally at least one coupler component as the oxidation dye precursors. The actual dyes may be formed by the developer components with one another, but preferably with coupler components. The coloring agents therefore preferably contain at least one oxidation dye precursor of the developer type and at least one oxidation dye precursor of the coupler type. The oxidation dye precursors are preferably used in a quantity of 0.005 to 20 wt. %, preferably of 0.05 to 5 wt. % and particularly preferably of 0.1 to 5 wt. %, in each case relative to the ready-to-use oxidation coloring agent. The developer and coupler components may be used in free form. For substances bearing amino groups, it may, however, be preferable to use them in salt form, in particular in the form of the hydrochlorides and hydrobromides or sulfates.

Developer components and coupler components may be used in approximately molar quantities relative to one another. While molar use has also proven convenient, a certain excess of individual oxidation dye precursors is not disadvantageous, such that developer components and coupler components may be contained in a molar ratio of 3:1 to 1:3, in particular 2:1 to 1:1.

Suitable oxidation dye precursors of the developer type are p-phenylenediamine and the derivatives thereof. Preferred p-phenylenediamines are selected from p-phenylenediamine, p-tolylenediamine, 2-chloro-p-phenylenediamine, 2,3-dimethyl-p-phenylenediamine, 2,6-dimethyl-p-phenylenediamine, N,N-bis-(2'-hydroxyethyl)-p-phenylenediamine, 2-(2-hydroxyethyl)-p-phenylenediamine, 2-(1,2-dihydroxyethyl)-p-phenylenediamine, N-(2-hydroxypropyl)-p-phenylenediamine, N-(4'-aminophenyl)-p-phenylenediamine, 2-methoxymethyl-p-phenylenediamine, N-phenyl-p-phenylenediamine, 2-(2-hydroxyethyl)-p-phenylenediamine and N-(4-amino-3-methylphenyl)-N-[3-(1H-imidazol-1-yl)propyl]amine and the physiologically acceptable salts thereof.

It may furthermore be preferred to use compounds which contain at least two aromatic nuclei which are substituted with amino and/or hydroxyl groups as the developer component. Preferred binuclear developer components are selected from N,N'-bis-(2-hydroxyethyl)-N,N'-bis-(4'-aminophenyl)-1,3-diaminopropan-2-ol, N,N'-bis-(4'-aminophenyl)-1,4-diazacycloheptane, and bis-(2-hydroxy-5-aminophenyl)methane and the physiologically acceptable salts thereof.

It may furthermore be preferred to use a p-aminophenol derivative or one of the physiologically acceptable salts thereof as the developer component. Preferred p-aminophenols are p-aminophenol, N-methyl-p-aminophenol, 4-amino-3-methylphenol, 4-amino-2-aminomethylphenol, 4-amino-2-(1,2-dihydroxyethyl)phenol and 4-amino-2-(diethylaminomethyl)phenol and the physiologically acceptable salts thereof.

The developer component may furthermore be selected from o-aminophenol and the derivatives thereof, preferably from 2-amino-4-methylphenol, 2-amino-5-methylphenol, 2-amino-4-chlorophenol and/or the physiologically acceptable salts thereof.

The developer component may furthermore be selected from heterocyclic developer components, such as for example pyrimidine derivatives, pyrazole derivatives, pyrazolopyrimidine derivatives or the physiologically acceptable salts thereof. Preferred pyrimidine derivatives are the compounds 2,4,5,6-tetraaminopyrimidine, 4-hydroxy-2,5,6-triaminopyrimidine and the physiologically acceptable salts thereof. A preferred pyrazole derivative is 4,5-diamino-1-(2-hydroxyethyl)pyrazole and the physiologically acceptable salts thereof. Pyrazolo[1,5-a]pyrimidines are in particular preferred as pyrazolopyrimidines.

Particularly preferred developer components are p-tolylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and the physiologically acceptable salts thereof.

The coupler components used may be m-phenylenediamine derivatives, naphthols, resorcinol and resorcinol derivatives, pyrazolones and m-aminophenol derivatives.

Coupler components which are preferred according may include:
  (i) m-aminophenol and the derivatives thereof, in particular 3-aminophenol, 5-amino-2-methylphenol, 3-amino-2-chloro-6-methylphenol, 5-amino-4-chloro-2-methylphenol, 5-(2'-hydroxyethyl)-amino-2-methylphenol and 2,4-dichloro-3-aminophenol;
  (ii) o-aminophenol and the derivatives thereof, such as 2-amino-5-ethylphenol;
  (iii) m-diaminobenzene and the derivatives thereof such as for example 2,4-diaminophenoxyethanol, 1,3-bis-(2',4'-diaminophenoxy)propane, 1-methoxy-2-amino-4-(2'-hydroxyethylamino)benzene, 2,6-bis-(2'-hydroxyethylamino)-1-methylbenzene, 2-({3-[(2-hydroxyethyl)amino]-4-methoxy-5-methylphenyl}amino)ethanol and 2-({3-[(2-hydroxyethyl)amino]-2-methoxy-5-methylphenyl}amino)ethanol;

(iv) o-diaminobenzene and the derivatives thereof;
(v) di- or trihydroxybenzene derivatives, in particular resorcinol, 2-chlororesorcinol, 4-chlororesorcinol, 2-methylresorcinol and 1,2,4-trihydroxybenzene;
(vi) pyridine derivatives, in particular 3-amino-2-methylamino-6-methoxypyridine, 2,6-diaminopyridine, 2,6-dihydroxy-3,4-dimethylpyridine, 2-amino-3-hydroxypyridine and 3,5-diamino-2,6-dimethoxypyridine;
(vii) naphthalene derivatives, such as 1-naphthol and 2-methyl-1-naphthol;
(viii) morpholine derivatives, such as 6-hydroxybenzomorpholine;
(ix) quinoxaline derivatives;
(x) pyrazole derivatives, such as 1-phenyl-3-methylpyrazol-5-one;
(xi) indole derivatives, such as 6-hydroxyindole;
(xii) pyrimidine derivatives; or
(xiii) methylenedioxybenzene derivatives, such as 1-(2'-hydroxyethyl)-amino-3,4-methylenedioxybenzene, and the physiologically acceptable salts thereof.

Coupler components which are particularly preferred may include resorcinol, 2-methylresorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene and 1-naphthol and a physiologically acceptable salt thereof.

In one example, the agents may contain at least one precursor of a nature-analogous dye. Precursors of nature-analogous dyes may preferably be those indoles and indolines which comprise at least one hydroxyl or amino group, preferably as a substituent on the six-membered ring. Particularly preferred derivatives of indoline are 5,6-dihydroxyindoline and 2,3-dioxoindoline (isatin) and the physiologically acceptable salts thereof. One particularly preferred derivative of indole is 5,6-dihydroxyindole and the physiologically acceptable salts thereof. The agents preferably contain the indole or indoline derivatives in a quantity of 0.05 to 10 wt. %, preferably 0.2 to 5 wt. %, in each case relative to the total weight thereof.

The agents may furthermore contain at least one substantive dye. These are dyes which key directly to the hair and may not need an oxidative process to develop the color. Examples of substantive dyes include nitrophenylenediamines, nitroaminophenols, azo dyes, anthraquinones or indophenols. Substantive dyes may be subdivided into anionic, cationic and nonionic substantive dyes. The substantive dyes in each case are preferably used in a quantity of 0.001 to 20 wt. %, in particular of 0.05 to 5 wt. %, in each case relative to the total preparation for use. The total quantity of substantive dyes preferably amounts to at most 20 wt. %.

Preferred anionic substantive dyes may be the compounds known by the names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromophenol blue. Preferred cationic substantive dyes may be cationic triphenylmethane dyes, such as Basic Blue 7, Basic Blue 26, Basic Violet 2 and Basic Violet 14, aromatic systems which are substituted with a quaternary nitrogen group, such as Basic Yellow 57, Basic Red 76, Basic Blue 99, Basic Brown 16 and Basic Brown 17 and HC Blue 16, and Basic Blue 347, Basic Yellow 87, Basic Orange 31 and Basic Red 51. Preferred nonionic substantive dyes may include HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2'-hydroxyethyl)amino-4,6-dinitrophenol, 4-[(2-hydroxyethypamino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol. Naturally occurring dyes may furthermore also be used as substantive dyes, such as are present for example in henna red, henna neutral, henna black, chamomile flowers, sandalwood, black tea, walnut, alder buckthorn bark, sage, logwood, madder root, catechu and alkanet root.

As a further feature, the agents may contain a carrier base combination. The carrier base combination comprises at least one fatty substance of formula (I),

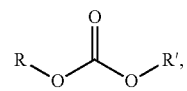
(I)

at least one nonionic surfactant of formula (II),

(II), and at least one cationic polymer, amphoteric polymer, or combinations thereof.

Compounds of formula (I) in which R and R' mutually independently denote a saturated or unsaturated $C_6$-$C_{20}$ alkyl chain may be used as the fatty substance.

The $C_6$-$C_{22}$ alkyl chain may here be unbranched or comprise branches, in particular if they are derived from Guerbet alcohols. Examples of $C_6$-$C_{22}$ alkyl chains include n-hexyl, n-heptyl, n-octyl, n-nonyl, n-decyl, i-decyl, n-dodecyl (lauryl), n-tridecyl, i-tridecyl, n-tetradecyl (myristyl), n-pentadecyl, n-hexadecyl (cetyl), n-heptadecyl, n-octadecyl (stearyl), n-eicosyl (arachidyl), n-docosanyl (behenyl), 2-ethylhexyl, 2-butyloctyl, 2-hexyldecyl, 2-octyldodecyl, 2-heptylundecyl and oleyl, linolenyl, linoleyl, palmitoleyl, erucyl and brassidyl. It may be preferred to use compounds based on alkyl chain mixtures, in particular if the alkyl chains are obtained as mixtures from their manufacturing method. Examples are cetearyl ($C_{16}$/$C_{18}$ mixture), coco alkyl (alkyl chain mixture from coco fat fatty acid cut), olive alkyl (alkyl chain mixture from olive oil fatty acid cut) or tallow alkyl (alkyl chain mixture from tallow fatty acid cut).

In preferred fatty substances of formula (I), R and R' in each case may mutually independently denote a saturated or unsaturated $C_6$-$C_{14}$ alkyl chain, preferably a $C_6$-$C_{10}$ alkyl chain.

In one example, the agent may contain di-n-octyl carbonate and/or di-(2-ethylhexyl)carbonate as the preferred fatty substance of formula (I).

The agent preferably contains a total proportion of fatty substances of 0.05 to 8.5 wt. %, preferably of 0.1 to 6 wt. %, in particular of 0.2 to 4 wt. % and more preferably of 0.3 to 2.5 wt. %, in each case relative to the total weight of the agent.

The agent may contain at least one nonionic surfactant of formula (II), $$R1\text{-}O\text{-}[G]_p \qquad (II),$$

in which R1 denotes a saturated or unsaturated $C_6$-$C_{22}$ alkyl chain, G denotes a sugar residue with 5 or 6 carbon atoms and p denotes a number from 1 to 10.

Compounds of formula (II) may be in particular alkyl polyglucosides. The sugar residue G is here derived from aldoses or ketoses with 5 or 6 carbon atoms, preferably from glucose. The index value "p" in the general formula (II) indicates the degree of polymerization (DP), i.e. the distribution of mono- and polyglucosides, and denotes a number between 1 and 10. While "p" may always be integral in the individual molecule and in this case may primarily assume the values p=1 to 6, the value "p" for a specific alkyl polyglucoside is a calculated value determined by analysis. Alkyl polyglucosides with an average degree of oligomerization p of 1.1 to 3.0 may be preferably used. Alkyl polyglucosides having a degree of polymerization (i.e. their p number) which is less than 1.7 and in particular between 1.2 and 1.4 are preferred from an application standpoint.

The alkyl residue R1 in formula (II) may be derived from primary alcohols having 6 to 11, preferably 8 to 10 carbon atoms. Examples include caproic alcohol, caprylic alcohol, capric alcohol and undecyl alcohol and the technical mixtures thereof, as are, for example, obtained from the hydrogenation of technical fatty acid methyl esters or in the course of hydrogenation of aldehydes from Roelen's oxo synthesis. Preferred alkyl polyglucosides are those of a $C_8$-$C_{10}$ chain length (DP=1 to 3) which occur as forerunnings in the distillative separation of technical $C_8$-$C_{18}$ coco fatty alcohol and may be contaminated with a proportion of less than 6 wt. % of $C_{12}$ alcohol and alkyl polyglucosides based on technical $C_{9/11}$ oxo alcohols (DP=1 to 3).

The alkyl residue R1 may furthermore also be derived from primary alcohols having 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and the technical mixtures thereof, which may be obtained as described above. Preferred alkyl oligoglucosides are those based on hardened $C_{12/14}$ coco alcohol with a DP of 1 to 3.

R1 preferably denotes a coco alkyl group, a stearyl group, a cetyl group, a lauryl group, mixtures of $C_8$-$C_{10}$ alkyl groups, mixtures of $C_{12/14}$ alkyl groups and/or mixtures thereof.

In a preferred example, the agent may contain as the nonionic surfactant at least one compound of formula (II), in which R1 denotes a $C_{12}$ alkyl group, a $C_{14}$ alkyl group or a coco alkyl group and G denotes a glucose residue.

Alkyl polyglucosides of formula (II) which are particularly suitable according to the invention are distributed under the INCI name Coco Glucoside and the trade name Plantacare® 818 UP or under the INCI name Lauryl Glucoside and the trade name Plantacare® 1200 UP.

It is preferred to use the alkyl polyglucosides of formula (II) in a proportion of 0.1 to 12 wt. %, preferably of 0.5 to 10 wt. %, particularly preferably of 1.0 to 9 wt. % and more preferably of 1.5 to 7.5 wt. %, in each case relative to the total weight of the agent.

The agent may contain at least one cationic polymer, at least one amphoteric polymer, or combinations thereof as an additional ingredient.

As used in the present specification and in the appended claims, the term "cationic polymers" may refer to polymers which comprise a group in the main and/or side chain which is "temporarily" or "permanently" cationic.

Examples of suitable polymers with quaternary amine groups include the polymers described in the CTFA Cosmetic Ingredient Dictionary under the names Polyquaternium, such as methylvinylimidazolium chloride/vinylpyrrolidinone copolymer (Polyquaternium-16), quaternized vinylpyrrolidinone/dimethylaminoethyl methacrylate copolymer (Polyquaternium-11; tradenames Gafquat 755 N and 734). Copolymers of vinylpyrrolidinone and imidazolimine methochloride (Luviquat HM 550) and vinylpyrrolidinone/methacrylamidopropyltrimethylammonium chloride copolymers (Gafquat HS 100) are likewise suitable. Likewise suitable are homopolymers, such as poly(methacryloyloxyethyltrimethylammonium chloride) (INCI name Polyquaternium-37) with the trade names Rheocare CTH, Synthalen CR, Salcare SC 95 and Salcare SC 96.

Further preferred cationic polymers are cationized honey, for example the commercial product Honeyquat® 50, polymeric dimethyldiallylammonium salts and the copolymers thereof with esters and amides of acrylic acid and methacrylic acid, such as for example Merquat 100 (poly(dimethyldiallylammonium chloride)) and Merquat 550 (dimethyldiallylammonium chloride/acrylamide copolymer), vinylpyrrolidinone/vinylmethylimidazolium chloride copolymers, such as Luviquat FC 370, FC 905 and HM 552 (Polyquaternium-16), vinylpyrrolidinone/vinylmethylimidazolium methylsulfate copolymers, such as Luviquat UltraCare (Polyquaternium-44), vinylpyrrolidinone/vinylcaprolactam/vinylmethylimidazolium methylsulfate copolymers, such as Luviquat Hold (Polyquaternium-46), Polyquaternium-68, quaternized polyvinyl alcohol, vinylpyrrolidinone/vinylcaprolactam/acrylate terpolymers, such as for example Aquaflex SF 40, and the polymers with quaternary nitrogen atoms in the polymer main chain known by the names Polyquaternium-2, Polyquaternium-17, Polyquaternium-18, Polyquaternium-27 and Polyquaternium-59.

Further suitable cationic polymers may be derived from natural polymers, in particular cationic derivatives of polysaccharides, for example cationic derivatives of cellulose, starch or guar. Chitosan and chitosan derivatives are furthermore suitable.

Examples of cationic celluloses are the polymers with the trade names Polymer JR 400 (INCI name Polyquaternium-10), Polymer LM-200 (INCI name Polyquaternium-24), Celquat H 100 and Celquat L 200 (Polyquaternium-4), Soft-CAT SX 400 X, SL 5, SL 100 and SK-MH (Polyquaternium-67) and Mirustyle CP (Polyquaternium-72).

Suitable cationic guar derivatives are available for example under the trade names Jaguar®, N-Hance®, Cosmedia® Guar and AquaCat® (INCI name Guar Hydroxypropyltrimonium Chloride).

A further particularly suitable cationic natural polymer is chitosan, optionally also the quaternized, alkylated and/or hydroxyalkylated derivatives thereof. Examples of suitable commercial products that may be available include Flonac® or Kytamer® PC and Hydagen® CMF, Hydagen® HCMF and Chitolam® NB/101.

Amphoteric polymers are distinguished in that, in addition to cationic structural units, they also comprise anionic structural units, for the most part as deprotonated carboxylic acid or sulfonic acid.

Examples of suitable amphoteric polymers are in particular Polyquaternium-22 (copolymer of diallyldimethylammonium chloride and acrylic acid), Polyquaternium-39 (copolymer of diallyldimethylammonium chloride, acrylamide and acrylic acid) and Polyquaternium-86 (copolymer of vinylpyrrolidinone, vinylmethylimidazolium chloride, vinylimidazole and methacrylic acid). Preferred cationic and/or amphoteric polymers are distinguished in that they have been produced by polymerization in the presence of specific cationic monomers of formula (III)

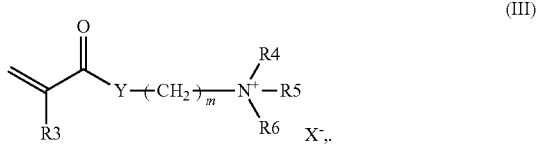

As a consequence, the polymer comprises units in its structure which originate from compounds of formula (III).

In the compounds of formula (III), R3 may denote a hydrogen atom or a $CH_3$ group, Y may denote O or NH, "m" may denote a number from 2 to 6, and R4, R5 and R6 in each case mutually independently may denote an optionally saturated or unsaturated $C_1$-$C_{22}$ alkyl chain.

A further example is therefore an agent which is characterized in that it comprises as a cationic and/or amphoteric polymer, at least one polymer which comprises a compound of formula (III) as a monomer,

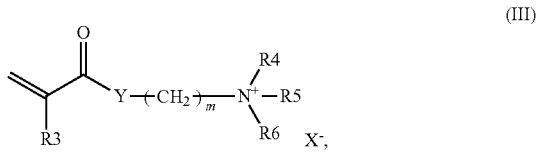

in which, R3 denotes a hydrogen atom or a $CH_3$ group, Y denotes O or NH, "m" denotes a number from 2 to 6, $X^-$ denotes a physiologically acceptable anion, and R4, R5 and R6 in each case mutually independently denote an optionally saturated or unsaturated $C_1$-$C_{22}$ alkyl chain.

The optionally saturated or unsaturated $C_1$-$C_{22}$ alkyl chain may here, once the number of C atoms is at least 3 carbon atoms, be unbranched or comprise branches, in particular if they are derived from Guerbet alcohols. Examples of $C_1$-$C_{22}$ alkyl chains according to the invention are methyl, ethyl, propyl, i-propyl, n-butyl, i-butyl, tert.-butyl, n-pentyl, n-hexyl, n-heptyl, n-octyl, n-nonyl, n-decyl, i-decyl, n-dodecyl (lauryl), n-tridecyl, i-tridecyl, n-tetradecyl (myristyl), n-pentadecyl, n-hexadecyl (cetyl), n-heptadecyl, n-octadecyl (stearyl), n-eicosyl (arachidyl), n-docosanyl (behenyl), 2-ethylhexyl, 2-butyloctyl, 2-hexyldecyl, 2-octyldodecyl, 2-heptylundecyl and oleyl, linolenyl, linoleyl, palmitoleyl, erucyl and brassidyl. It may be preferred to use compounds based on alkyl chain mixtures, in particular if the alkyl chains are obtained as mixtures from their manufacturing method. Examples are cetearyl ($C_{16}$/$C_{18}$ mixture), coco alkyl (alkyl chain mixture from coco fat fatty acid cut), olive alkyl (alkyl chain mixture from olive oil fatty acid cut) or tallow alkyl (alkyl chain mixture from tallow fatty acid cut).

It may be preferred for at most one of substituents R4, R5 and R6 to be an alkyl chain with more than 2 carbon atoms. R4, R5 and R6 particularly preferably, however, in each case denote methyl.

Examples of cationic or amphoteric polymers (C) according to the invention are:

(i) Polyquaternium-11: copolymer of vinylpyrrolidone and 2-(ethyldimethylammonio)ethyl methacrylate ethylsulfate (R3=$CH_3$, Y=O, m=2, R4=R5=$CH_3$, R6=$C_2H_5$, $X^{-1}$=$EtOSO_3^-$);

(ii) Polyquaternium-28: copolymer of vinylpyrrolidone and methacrylaminopropyltrimethylammonium chloride (R3=$CH_3$, Y=NH, m=3, R4=R5=R6=$CH_3$, $X^-$=$Cl^-$);

(iii) Polyquaternium-37: homopolymer of 2-(trimethylammonio)ethyl methacrylate chloride (R3=$CH_3$, Y=O, m=2, R4=R5=R6=$CH_3$, $X^-$=$Cl^-$);

Polyquaternium-55: terpolymer of vinylpyrrolidone, N-(3-dimethylamino)propyl methacrylamide and methacrylaminopropyl(lauryl)dimethylammonium chloride (R3=$CH_3$, Y=NH, m=3, R4=R5=$CH_3$, R6=$C_{12}H_{25}$, $X^-$=$Cl^-$);

(iv) Polyquaternium-69: copolymer of vinylpyrrolidone, vinylcaprolactam, N-(3-dimethylamino)-propyl methacrylamide and methacrylaminopropyl(lauryl)dimethylammonium chloride (R3=$CH_3$, Y=NH, m=3, R4=R5=$CH_3$, R6=$C_{12}H_{25}$, $X^-$=$Cl^-$);

(v) Polyquaternium-85: copolymer of dimethylacrylamide, hydroxyethyl methacrylate and methacrylaminopropyltrimethylammonium chloride (R3=$CH_3$, Y=NH, m=3, R4=R5=R6=$CH_3$, $X^-$=$Cl^-$); and (vi) Polyquaternium-94: copolymer of acrylamide, dimethyldiallylammonium chloride and methacrylaminopropyltrimethylammonium chloride (R3=$CH_3$, Y=NH, m=3, R4=R5=R6=$CH_3$, $X^-$=$Cl^-$).

It may be particularly preferred for Y to denote an oxygen atom O. Furthermore, "m" may preferably denote a number 2 or 3.

A further example is therefore an agent which is characterized in that it comprises as a cationic and/or an amphoteric polymer at least one polymer which comprises a compound of formula (III) as a monomer, in which Y denotes O, "m" denotes 2 or 3 and R4, R5 and R6 in each case denote a $CH_3$ group.

The agent may particularly preferably contain at least Polyquaternium-37 as cationic and/or amphoteric polymer.

Particularly advantageous effects are achieved if the cationic and/or amphoteric polymer is used in a specific quantity in the agent, preferably in an amount of at least 0.05 wt. %. A further example of the agent is therefore an agent which is characterized in that the agent contains cationic and/or amphoteric polymers in a proportion of 0.05 to 7.5 wt. %, preferably of 0.1 to 5 wt. %, in particular of 0.12 to 1.5 wt. % and further preferably of 0.15 to 0.75 wt. %, in each case relative to the total weight of the agent.

In particular with regard to the color intensity, permanence and homogeneity of the coloring result and with regard to improving combability, it is advantageous to use the fatty substance and cationic and/or amphoteric polymers in a specific ratio to one another, advantageously in particular approximately in identical proportions by weight.

A further example of the agent is therefore an agent which is characterized in that it has a weight ratio of fatty substances and cationic and/or amphoteric polymers with a value of 3:1 to 1:3, preferably 2:1 to 1:2, particularly preferably 3:2 to 2:3.

It may be advantageous for the agent to contain additional fatty substances in addition to the fatty substances according to formula (I). It may be particularly advantageous for the agent to contain at least one additional fatty substance selected from fatty acid alkyl esters, fatty alkyl esters, fatty acid fatty alkyl esters and difatty alkyl ethers. As used in the present specification and in the appended claims, the term "fatty acid alkyl esters" may refer to carboxylic acid esters of fatty acids and mono- or polyhydroxy-$C_1$-$C_4$-alkanols.

Fatty acids may comprise 8 to 22 carbon atoms and may contain alkyl chains which, on the one hand, are branched or unbranched and, on the other hand, are saturated or unsaturated. Examples of fatty acids for the purposes of the invention include:
  (i) saturated, unbranched fatty acids, such as octanoic acid (caprylic acid), nonanoic acid (pelargonic acid), decanoic acid (capric acid), undecanoic acid, dodecanoic acid (lauric acid), tridecanoic acid, tetradecanoic acid (myristic acid), pentadecanoic acid, hexadecanoic acid (palmitic acid), heptadecanoic acid (margaric acid), octadecanoic acid (stearic acid), nonadecanoic acid, eicosanoic acid (arachidic acid), docosanoic acid (behenic acid);
  (ii) saturated, branched fatty acids, such as isooctanoic acid, isopalmitic acid, isostearic acid; and
  (iii) unsaturated, unbranched fatty acids, such as palmitoleic acid ((9Z)-hexadec-9-enoic acid), oleic acid ((9Z)-octadec-9-enoic acid), elaidic acid ((9E)-octadec-9-enoic acid), erucic acid ((13Z)-docos-13-enoic acid), linoleic acid ((9Z,12Z)-octadeca-9,12-dienoic acid), linolenic acid ((9Z,12Z,15Z)-octadeca-9,12,15-trienoic acid), eleostearic acid ((9Z,11E,13E)-octadeca-9,11,13-trienoic acid), arachidonic acid ((5Z,8Z,11Z,14Z)-icosa-5,8,11,14-tetraenoic acid).

Examples of mono- or polyhydroxy-$C_1$-$C_4$-alkanols are methanol, ethanol, propanol, isopropanol, ethylene glycol, propylene glycol, propane-1,3-diol, butane-1,2-diol, butane-1,3-diol, butane-1,4-diol, butane-2,3-diol and glycerol.

Preferred examples of fatty acid alkyl esters are isopropyl myristate, isopropyl palmitate, ethylene glycol distearate and fatty acid triglycerides, in particular triglyceride vegetable oils.

As used in the present specification and in the appended claims, the term "fatty alkyl esters" may refer to carboxylic acid esters of fatty alcohols and $C_2$-$C_6$ mono- or dicarboxylic acids. Fatty alcohols for the purposes of the invention are terminal alcohols which contain a saturated or unsaturated $C_6$-$C_{20}$ alkyl chain according to the above-stated definition. Suitable $C_2$-$C_6$ mono- or dicarboxylic acids are acetic acid, oxalic acid, maleic acid, succinic acid, adipic acid, isobutyric acid and propionic acid.

Examples of fatty alkyl esters which are preferred include di-(2-ethylhexyl)succinate, dioctyl adipate, di-(2-ethylhexyl) maleate, 2-ethylhexyl acetate, cetyl acetate and stearyl acetate. As used in the present specification and in the appended claims, the term "fatty acid fatty alkyl esters" may refer to carboxylic acid esters of fatty alcohols and fatty acids according to the above-stated definition.

Examples of fatty acid fatty alkyl esters which are preferred include myristyl myristate, myristyl palmitate, myristyl stearate, cetyl(2-ethylhexanoate), cetyl palmitate, decyl oleate, 2-ethylhexyl stearate, 2-ethylhexyl oleate and 2-ethylhexyl palmitate.

As used in the present specification and in the appended claims, the term "difatty alkyl ethers" may refer to dialkyl ethers in which both alkyl residues mutually independently denote a saturated or unsaturated $C_6$-$C_{20}$ alkyl chain according to the above-stated definition. $C_6$-$C_{14}$ alkyl chains are preferred.

Examples of difatty alkyl ethers which are preferred are diheptyl ether, dioctyl ether and dilauryl ether.

Where a further fatty substance is present, the total quantity of fatty substance in the agent should preferably not increase. One example of the agent is therefore characterized in that the agent comprises a total proportion of fatty substances and optionally further fatty substances of 0.05 to 8.5 wt. %, preferably of 0.1 to 6 wt. %, in particular of 0.2 to 4 wt. % and further preferably of 0.3 to 2.5 wt. %, in each case relative to the total weight of the agent.

In some examples, adding a specific amine oxide surfactant brings about additional improvement with regard to conditioning performance and combability.

Accordingly, another example of the agent is therefore characterized in that the agent additionally contains at least one amine oxide surfactant of formula (IV),

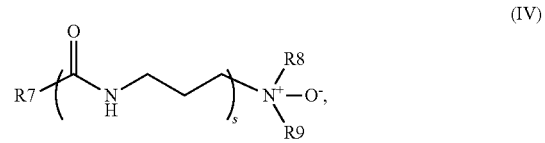

in which, R7 denotes a saturated or unsaturated $C_6$-$C_{22}$ alkyl chain, "s"

denotes the number 0 or 1, and R8 and R9 in each case mutually independently denote hydrogen, a $C_1$-$C_4$ alkyl chain or a $C_2$-$C_4$ hydroxyalkyl chain.

The above definition applies with regard to the saturated or unsaturated $C_6$-$C_{22}$ alkyl chain of residue R7. Preferred examples of a $C_1$-$C_4$ alkyl chain are methyl and ethyl, n-propyl or i-propyl, preferably methyl. Preferred examples of a $C_2$-$C_4$ hydroxyalkyl chain are 2-hydroxyethyl and 3-hydroxypropyl.

Examples of compounds of formula (IV) with R8=R9=hydrogen are the compounds with the INCI names Cocamine Oxide, Tallowamine Oxide, Decylamine Oxide, Lauramine Oxide, Myristamine Oxide, Palmitamine Oxide, Stearamine Oxide, Oleamine Oxide, Behenamine Oxide (each s=0) and Cocamidopropylamine Oxide, Tallowamidopropylamine Oxide, Decylamidopropylamine Oxide, Lauramidopropylamine Oxide, Myristamidopropylamine Oxide, Palmitamidopropylamine Oxide, Stearamidopropylamine Oxide, Oleamidopropylamine Oxide, Behenamidopropylamine Oxide (each s=1).

Examples of compounds of formula (IV) in which R8 and R9 denote a $C_2$-$C_4$ hydroxyalkyl chain are the compounds with the INCI names Dihydroxyethyl Cocamine Oxide, Dihydroxyethyl Tallowamine Oxide, Dihydroxyethyl Lauramine Oxide, Dihydroxyethyl Stearamine Oxide.

R8 and R9 may preferably in each case denote methyl. Further preferably, "s" denotes 0. Examples of particularly preferred compounds of formula (IV) in which R8 and R9 denote methyl, are the compounds Dimethyl Cocamine Oxide, Dimethyl Tallowamine Oxide, Dimethyl Decylamine Oxide, Dimethyl Lauramine Oxide, Dimethyl Myristamine Oxide, Dimethyl Palmitamine Oxide, Dimethyl Stearamine Oxide, Dimethyl Oleamine Oxide and Dimethyl Behenamine Oxide together with Dimethyl Cocamidopropylamine Oxide, Dimethyl Tallowamidopropylamine Oxide, Dimethyl Decylamidopropylamine Oxide, Dimethyl Lauramidopropylamine Oxide, Dimethyl Myristamidopropylamine Oxide, Dimethyl Palmitamidopropylamine Oxide and Dimethyl Stearamidopropylamine Oxide.

The agents may contain amine oxide surfactants of formula (IV) in a proportion of 0.01 to 5 wt. %, preferably 0.05 to 2.5 wt. %, further preferably 0.1 to 1.5 wt. % and particularly preferably 0.15 to 1.0 wt. %, relative to the total weight of the agent.

In the case of oxidative coloring, the color may in principle be developed with atmospheric oxygen. Preferably, however, a chemical oxidizing agent is used, particularly when the intention is to lighten human hair as well as color it.

Another example of the agent is therefore an agent which additionally contain an oxidizing agent selected from hydrogen peroxide and the solid addition products thereof onto organic and inorganic compounds. Solid addition products which may be used are in particular addition products onto urea, melamine, polyvinylpyrrolidinone and sodium borate.

Hydrogen peroxide is preferably used as the oxidizing agent. The quantity of hydrogen peroxide in the ready-to-use agent preferably amounts to 0.5 to 12 wt. %, preferably 0.8 to 6 wt. %, in each case relative to the ready-to-use agent.

The ready-to-use agent may be prepared shortly prior to use from a color modification preparation and an oxidizing agent preparation.

However, the color modifying agent as an oxidation coloring agent may also be applied onto the hair together with a catalyst which activates the oxidation of the dye precursors, for example by atmospheric oxygen. Such catalysts are for example specific enzymes, iodides, quinones or metal ions.

It may further be advantageous for the agent, in particular the oxidizing agent preparations, to contain at least one stabilizer or complexing agent. Chelate complexing agents which are preferred are for example polycarboxylic acids, nitrogenous mono- or polycarboxylic acids, in particular ethylenediaminetetraacetic acid (EDTA), ethylenediaminedisuccinic acid (EDDS) and nitrilotriacetic acid (NTA), geminal diphosphonic acids, in particular 1-hydroxyethane-1,1-diphosphonic acid (HEDP), aminophosphonic acids such as ethylenediaminetetra(methylenephosphonic acid) (EDTMP) and diethylenetriaminepenta(methylenephosphonic acid) (DTPMP), phosphonopolycarboxylic acids such as 2-phosphonobutane-1,2,4-tricarboxylic acid as well as cyclodextrins, alkali metal stannates (sodium stannate), alkali metal pyrophosphates (tetrasodium pyrophosphate, disodium pyrophosphate), alkali metal phosphates (sodium phosphate), and phosphoric acid. The agents preferably contain complexing agents in an amount of 0.01 to 3 wt. %, preferably 0.05 to 1 wt. %, in each case relative to the total weight of the agent.

The agents may be preferably formulated as flowable preparations. These include in particular emulsions, suspensions and gels, particularly preferably emulsions. The flowable preparations may preferably additionally contain an emulsifier or a surfactant as a surface-active substance, wherein surface-active substances, may refer to surfactants or emulsifiers and are selected from anionic, cationic, amphoteric, zwitterionic and nonionic surfactants.

Anionic surfactants which are suitable in preparations may be any anionic surface-active substances suitable for use on the human body. These may be characterized by an anionic water-solubilizing group such as for example a carboxylate, sulfate, sulfonate or phosphate group and a lipophilic alkyl group with approximately 8 to 30 C atoms, preferably 8 to 24 C atoms. The molecule may additionally contain glycol or polyglycol ether groups, ester, ether and amide groups and hydroxyl groups. Preferred anionic surfactants are soaps, alkyl sulfates, alkyl ether sulfates and ether carboxylic acids with 10 to 18 C atoms in the alkyl group and up to 12 glycol ether groups per molecule. Zwitterionic surfactants are those surface-active compounds which bear at least one quaternary ammonium group and at least one carboxylate, sulfonate or sulfate group per molecule. Particularly suitable zwitterionic surfactants are "betaines" such as N-alkyl-N,N-dimethylammonium glycinates, N-acylaminopropyl-N,N-dimethylammonium glycinates and 2-alkyl-3-carboxymethyl-3-hydroxyethylimidazolines together with cocoacylaminoethylhydroxyethylcarboxymethyl glycinate. One preferred zwitterionic surfactant is the fatty acid amide derivative known by the INCI name Cocamidopropyl Betaine. In a further example, the agent may contain at least one amphoteric surfactant. As used in the present specification and in the appended claims, the term "amphoteric surfactants" may refer to those surface-active compounds which, in addition to a $C_8$-$C_{24}$ alkyl or acyl group, contain at least one free amino group and at least one COOH or $SO_3H$ group per molecule and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids. Particularly preferred amphoteric surfactants are distributed under the INCI name Disodium Cocoamphodipropionate with the trade names Miranol® C2M SF conc. (Rhodia®), Amphoterge® K-2 (Lonza®) and Monateric® CEM-38 (Unichema®) and INCI name Disodium Cocoamphodiacetate with the trade names Dehyton® (Cognis®), Miranol® C2M (Rhodia®) and Ampholak® XCO 30 (Akzo Nobel®). It may be furthermore advantageous for the coloring or lightening agents to contain nonionogenic interfacially active substances. Nonionic surfactants contain as hydrophilic group for example a polyol group, a polyalkylene glycol ether group or a combination of a polyol group and polyglycol ether group. Further additional preferred nonionic surfactants include alkylene oxide addition products onto saturated linear fatty alcohols and fatty acids with in each case 2 to 30 mol of ethylene oxide per mol of fatty alcohol or fatty acid respectively. Preparations having excellent properties are likewise obtained if they contain fatty acid esters of ethoxylated glycerol as the nonionic surfactants. The anionic, nonionic, amphoteric or zwitterionic surfactants are used in total quantities of 0.1 to 45 wt. %, preferably 1 to 30 wt. % and particularly preferably of 1 to 15 wt. %, relative to the total quantity of the ready-to-use agent.

Preference is likewise given to cationic surfactants of the quaternary ammonium compound, ester quat and alkylamidoamine type. Preferred quaternary ammonium compounds are ammonium halides, such as alkyltrimethylammonium chlorides, dialkyldimethylammonium chlorides and trialkylmethylammonium chlorides, and the imidazolinium compounds known under the INCI names Quaternium-27 and Quaternium-83. The long alkyl chains of the above-stated surfactants preferably comprise 10 to 18 carbon atoms. Further cationic surfactants which are usable are quaternized protein hydrolysates. Alkylamidoamines are conventionally produced by amidating natural or synthetic fatty acids and fatty acid cuts with dialkylaminoamines. Tegoamid® S 18 (stearamidopropyldimethylamine) is one compound from this group of substances which is suitable. Ester quats are substances which contain both at least one ester function and at least one quaternary ammonium group as a structural element. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. Such products are distributed under the trademarks Stepante®x, Dehyquart® and Armocare®. The agents used according to the invention preferably contain the cationic surfactants in quantities of 0.05 to 10 wt. %, relative to the total agent. Quantities of 0.1 to 5 wt. % are particularly preferred.

The agents may contain further active ingredients, auxiliary substances and additives, such as for example nonionic polymers (such as vinylpyrrolidinone/vinyl acrylate copolymers, polyvinylpyrrolidinone, vinylpyrrolidinone/vinyl acetate copolymers, polyethylene glycols and polysiloxanes); anionic polymers (such as polyacrylic acids, crosslinked polyacrylic acids, vinyl acetate/crotonic acid copolymers, vinylpyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-tert.-butylacrylamide terpolymers); thickeners (agar-agar, guar gum, alginates, xanthan gum, gum arabic, karaya gum, locust bean flour, linseed gums, dextrans, cellulose derivatives, for example methylcellulose, hydroxyalkylcellulose and carboxymethylcellulose, starch fractions and derivatives such as amylose, amylopectin and dextrins, clays such as for example bentonite or completely synthetic hydrocolloids such as for example polyvinyl alcohol); hair-conditioning compounds (such as phospholipids, such as soy lecithin, egg lecithin, cephalins and silicone oils); additional protein hydrolysates of plant or animal origin (such as elastin, collagen, keratin, milk protein, soy protein and wheat protein hydrolysates, the condensation products thereof with fatty acids and quaternized protein hydrolysates); perfume oils, dimethyl isosorbide and cyclodextrins; active substances which improve fiber structure (such as mono-, di- and oligosaccharides, glucose, maleic acid and lactic acid); defoamers such as silicones (dimethicone); dyes for coloring the agent; antidandruff active ingredients (such as piroctone olamine, zinc omadine and climbazole); light stabilizers (such as derivatized benzophenones, cinnamic acid derivatives and triazines); active substances (pantolactone, allantoin, pyrrolidonecarboxylic acids and the salts thereof as well as bisabolol); vitamins, provitamins and vitamin precursors, in particular those of groups A, B3, B5, B6, C, E, F and H; plant extracts; cholesterol; consistency providers (such as sugar esters, polyol esters or polyol alkyl ethers); further fats and waxes (fatty alcohols, beeswax, montan wax and paraffins); swelling and penetrating substances (glycerol, propylene glycol monoethyl ether, carbonates, hydrogencarbonates, guanidines, ureas and primary, secondary and tertiary phosphates); opacifiers (latex, styrene/PVP and styrene/acrylamide copolymers); pearlescent agents (ethylene glycol monostearate and PEG-3 distearate); propellants such as propane/butane mixtures, $N_2O$, dimethyl ether, $CO_2$ and air; antioxidants.

These further substances may be selected according to the desired properties of the preparations. The preparations preferably contain the further active ingredients, auxiliary substances and additives in quantities of 0.01 to 25 wt. %, in particular 0.05 to 15 wt. %, relative to the total quantity of the ready-to-use agent.

The agents may preferably have a pH value in the range from 4 to 12. In the case of oxidation coloring agents, the coloring agents may be used in a weakly alkaline environment, preferably at a pH value in the range from 8.0 to 10.5. The pH values for are pH values which were measured at a temperature of 22° C.

A person skilled in the art may be familiar with conventional acidifying and alkalizing agents for adjusting the pH value. Alkalizing agents which are usable for adjusting the pH value may be selected from inorganic salts, in particular of alkali metals and alkaline earth metals, organic alkalizing agents, in particular amines, basic amino acids and alkanolamines, and ammonia. Acidifying agents which are preferred may be edible acids, such as for example citric acid, acetic acid, malic acid or tartaric acid, together with dilute mineral acids. Organic alkalizing agents which are usable may be preferably selected from alkanolamines, selected from 2-aminoethan-1-ol (monoethanolamine), 2-amino-2-methylpropan-1-ol, 2-amino-2-methylpropane-1,3-diol and triethanolamine. Basic amino acids are preferably selected from arginine and lysine. Inorganic alkalizing agents which are usable may be preferably selected from the group formed of sodium hydroxide, potassium hydroxide, calcium hydroxide, barium hydroxide, sodium phosphate, potassium phosphate, sodium silicate, potassium silicate, sodium carbonate and potassium carbonate, preferably sodium hydroxide and/or potassium hydroxide. Finally, a further preferred alkalizing agent is ammonia.

The agents may be produced from two or more separately packaged preparations directly prior to use. This may be appropriate for separating incompatible ingredients in order to avoid a premature reaction. Separation into multicomponent systems may be appropriate with incompatible ingredients. In such systems, the ready-to-use agent may be produced by the consumer directly prior to use by mixing the components. This procedure may be particularly preferred in the case of an oxidative coloring agent, in which the oxidation dye precursors are initially separated from an oxidizing agent preparation, preferably containing hydrogen peroxide.

In principle, the active substances may be incorporated both into the dye preparation with the oxidation dye precursors and into the oxidizing agent preparation. The carrier base combination of the fatty substance of formula (I), the non-ionic surfactant of formula (II), and the cationic and/or amphoteric polymer may be preferably formulated together with the oxidation dye precursor in a dye preparation and may be mixed with the oxidizing agent preparation immediately prior to use.

To this end, the dye preparation and oxidizing agent preparation may be preferably provided in two containers which are packaged separately from one another, but may advantageously be distributed in a common packaging unit.

As used in the present specification and in the appended claims, a "container" may refer to a package assuming the form of an optionally reclosable bottle, a tube, a can, a small pouch, a sachet or similar packages. The present specification does not place any limits on the material of the package. The packages are, however, preferably made of glass or plastics material.

The agents may be used in a method for modifying the color of human hair. An agent may be applied onto the hair and left on the hair for a period of 3 to 45 minutes, preferably 5 to 30 minutes. The hair may then be rinsed with water and/or a commercial shampoo.

The application and exposure temperature of the color modifying preparation may range from room temperature to 45° C. The action of the color modifying preparation may optionally be enhanced by external input of heat, such as for example by means of a heat cap. The preferred period of exposure of the color modifying preparation on the keratinic fibers is 3 to 45 minutes, preferably 5 to 30 minutes. Once the period of exposure has elapsed, the residual color modifying agent may be washed off the keratinic fibers with the assistance of a cleaning preparation or water. Once the agent has been washed out, the keratinic fibers are optionally dried with a hand towel or a hair dryer. The color modifying preparation may be applied by hand by the user. Personal protective clothing is preferably worn, in particular suitable safety gloves, for example of plastics or latex for single use (disposable gloves) and optionally an apron. It is, however, also possible to apply the color modifying agent onto the keratinic fibers with an application aid.

Using the agents on human hair makes it possible to combine coloring human hair with improved hair care and/or improved combability and/or increased color intensity and/or color retention, in particular with regard to hair washing. A further subject matter of the present specification is therefore the use of an agent when coloring human hair for improving hair care, for increasing color intensity and/or for improving color retention.

The above statements regarding the agents according to the present specification apply mutatis mutandis with regard to further preferred examples of the methods and uses according to the present specification.

EXAMPLES

Table 1 illustrates a number of coloring preparations according to the present specification. Unless otherwise stated, quantities are stated in proportions by weight.

TABLE 1

| Raw material | A | B | C | D | E | Comparison 1 | Comparison 2 |
|---|---|---|---|---|---|---|---|
| Ammonium Carbomer | 0.12 | 0.12 | 0.12 | 0.12 | 0.12 | 0.12 | 0.15 |
| Sodium Cetearyl Sulfate | 0.56 | 0.56 | 0.56 | 0.56 | 0.56 | 0.56 | 0.70 |
| Sodium Laureth Sulfate | — | — | — | — | — | 0.95 | 1.19 |
| Potassium Oleate | 0.30 | 0.30 | 0.30 | 0.30 | 0.30 | 0.30 | 0.38 |
| Lamesoft PO 65 | 1.50 | 1.50 | 1.50 | — | — | — | — |
| Aramox MCD W | — | — | — | 1.50 | 1.50 | — | — |
| Cutina GMS SE | 3.00 | 3.00 | 3.00 | 3.00 | 3.00 | 1.60 | 4.00 |
| Ethylene Glycol Distearate | — | — | — | — | — | 1.60 | — |
| 2-Octyldodecanol | — | — | — | — | — | 1.60 | 2.00 |
| Dioctyl Carbonate | 1.60 | — | — | — | — | — | — |
| Dioctyl Ether | — | 1.60 | — | — | 1.60 | — | — |
| Cetyl 2-ethylhexanoate | — | — | 1.60 | 1.60 | — | — | — |
| Cetearyl Alcohol | 9.90 | 9.90 | 9.90 | 9.90 | 9.90 | 9.60 | 12.00 |
| Ceteareth-20 | 2.40 | 2.40 | 2.40 | 2.40 | 2.40 | 2.40 | 3.00 |
| Phospholipid EFA | 0.10 | — | — | — | — | 0.1 | 0.1 |
| Triple C | 0.70 | 0.70 | 0.70 | 0.70 | 0.70 | — | — |
| L-Serine | 0.50 | 0.50 | 0.50 | 0.50 | 0.50 | 0.50 | 0.50 |
| EDTA, $Na_2$ | 0.20 | 0.20 | 0.20 | 0.20 | 0.20 | 0.20 | 0.20 |
| Merquat Plus 3330 | — | — | — | — | — | — | 1.50 |
| p-Tolylenediamine Sulfate | 0.84 | 0.84 | 0.84 | 0.84 | 0.84 | 0.84 | 0.84 |
| 4-Chlororesorcinol | 0.13 | 0.13 | 0.13 | 0.13 | 0.13 | 0.13 | 0.13 |
| 3-Aminophenol | 0.10 | 0.10 | 0.10 | 0.10 | 0.10 | 0.10 | 0.10 |
| Resorcinol | 0.23 | 0.23 | 0.23 | 0.23 | 0.23 | 0.23 | 0.23 |
| Ethanolamine | — | — | — | — | — | — | 0.30 |
| Potassium Hydroxide | — | — | — | — | — | 0.35 | — |
| Ascorbic Acid | — | — | — | — | — | 0.05 | 0.05 |
| Sodium Sulfite | 0.25 | 0.25 | 0.25 | 0.25 | 0.25 | 0.15 | 0.15 |
| Ammonia, 25 wt. % aqueous | 6.00 | 6.00 | 6.00 | 6.00 | 6.00 | 6.00 | 6.00 |
| Water | | | | Ad 100 | | | |

Table 2 illustrates a number of oxidizing agent preparations according to the present specification.

TABLE 2

| Raw material | II-1 | II-2 |
|---|---|---|
| Phosphoric Acid, 85 wt. % | 0.04 | — |
| EDTA, $Na_2$ | 0.15 | — |
| Disodium Pyrophosphate | 0.30 | 0.10 |
| Sodium Benzoate | 0.04 | 0.04 |
| Emulgade F | 2.20 | — |
| Dipicolinic Acid | — | 0.10 |
| Potassium Hydroxide | — | 0.10 |
| 1,2-Propanediol | — | 0.50 |
| Etidronic Acid | — | 0.15 |
| Paraffinum Liquidum | — | 2.00 |
| Cetearyl Alcohol | — | 3.40 |
| Ceteareth-20 | — | 1.00 |
| Hydrogen Peroxide, 50 wt. %, aqueous | 12.00 | 12.20 |
| Water | | Ad 100 |

Table 3 indicates a number of commercial products available for use in the preparation oxidizing agent preparation, or combinations thereof.

TABLE 3

| | |
|---|---|
| Lamesoft PO 65 | active substance content approx. 64-68%; INCI name: Coco Glucoside (20-40%), Glyceryl Oleate (20-40%), Aqua |
| Aramox MCD W | active substance content approx. 30%; INCI name: Dimethyl Cocamine Oxide |

TABLE 3-continued

| | |
|---|---|
| Cutina GMS SE | active substance content approx. 32-36%; INCI name: Glyceryl Stearate SE |
| Phospholipid EFA | active substance content approx. 30%; INCI name: Linoleamidopropyl PG-Dimonium Chloride Phosphate, Propylene Glycol (25%) |
| Merquat Plus 3330 | active substance content approx. 10%; INCI name: Polyquaternium-39 |
| Triple C | INCI name: Polyquaternium-37 (approx. 50%), Dioctyl Carbonate (approx. 48%), Lauryl Glucoside (approx. 2%) |
| Emulgade F | INCI name: Cetearyl Alcohol (70-85%), PEG-40 Castor Oil (10-20%), Sodium Cetearyl Sulfate (5-10%) |

Use—Coloring preparation (I) and oxidation preparation (II-1) were mixed in identical proportions by weight to form a ready-to-use coloring agent. For the coloring process, strands of hair (white, natural European hair (Kerling ENHw)) each weighing approx. 0.7 g had 4 times the quantity of this mixture for use applied to them. After a period of exposure of 30 minutes at 32° C., the strands were washed with water and dried with a hand towel.

The strands colored with agents according to the preparations A to E according to the present specification exhibited improved combability and better handling in the wet and dry states relative to strands colored with comparison preparation Comparison 1.

In a half-side test, test subjects had one half of their head hair colored under identical conditions with a mixture for use of comparison preparation Comparison 2 and oxidation preparation (II-2) and the other half with an mixture for use of the agent according to the invention D and oxidation preparation (II-1). The two halves were evaluated by hairdressers with regard to their conditioning state and their comb-ability and compared with one another.

The half colored with the agent according to the invention D exhibited an improved conditioning state which was manifested by easier comb-ability and improved handle in the wet and dry states.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for coloring keratinic fibers, comprising, in a cosmetically acceptable carrier:
at least one oxidation dye precursor, a precursor of a nature-analogous dye, a substantive dye, or combinations thereof; and
a carrier base combination, the carrier base combination comprising:
at least one fatty substance of formula (I), $$R\text{-}O\text{-}C(=O)\text{-}O\text{-}R', \quad (I)$$

in which R and R' in each case mutually independently denote a saturated or unsaturated $C_6$-$C_{22}$ alkyl chain;
at least one nonionic surfactant of formula (II), $$R1\text{-}O\text{-}[G]_p \quad (II),$$

in which R1 denotes a saturated or unsaturated $C_6$-$C_{22}$ alkyl chain, G denotes a sugar residue with 5 or 6 carbon atoms and p denotes a number from 1 to 10; and
at least one cationic polymer, at least one amphoteric polymer, or combinations thereof.

2. The agent of claim 1, in which the fatty substance of formula (I) comprises di-n-octyl carbonate, di-(2-ethylhexyl) carbonate, or combinations thereof.

3. The agent of claim 1, in which R1 of the nonionic surfactant of formula (II) comprises denotes a $C_{12}$ alkyl group, a $C_{14}$ alkyl group or a coco alkyl group and G denotes a glucose residue.

4. The agent of claim 1, in which the alkyl polyglucosides of formula (II) are present in a proportion of 0.1 to 12 wt. % of the total weight of the agent.

5. The agent of claim 1, in which the at least one cationic polymer, at least one amphoteric polymer, or combinations thereof comprise a compound of formula (III) as a monomer, $$\text{CH}_2=C(R3)\text{-}C(=O)\text{-}Y\text{-}(CH_2)_m\text{-}N^+(R4)(R5)(R6) \ X^-, \quad (III)$$

in which:
R3 denotes a hydrogen atom or a $CH_3$ group;
Y denotes O or NH;
m denotes a number from 2 to 6;
$X^-$ denotes a physiologically acceptable anion; and
R4, R5 and R6 mutually independently denote a saturated $C_1$-$C_{22}$ alkyl chain, an unsaturated $C_1$-$C_{22}$ alkyl chain, or combinations thereof.

6. The agent of claim 5, in which:
Y denotes O;
m denotes 2 or 3; and
R4, R5 and R6 each denote a $CH_3$ group.

7. The agent of claim 1, in which the at least one cationic polymer, the at least one amphoteric polymer, or combinations thereof comprise at least Polyquaternium-37.

8. The agent of claim 1, in which the at least one cationic polymer, the at least one amphoteric polymer, or combinations thereof form 0.05 to 7.5 wt. % of the total weight of the agent.

9. The agent of claim 1, in which a weight ratio of the at least one fatty substance to the at least one cationic polymer, at least one amphoteric polymer or combinations thereof is between 3:1 to 1:3.

10. The agent of claim 1, further comprising at least one additional fatty substance selected from fatty acid alkyl esters, fatty alkyl esters, fatty acid fatty alkyl esters and difatty alkyl ethers.

11. The agent of claim 10, in which the agent comprises a total proportion of fatty substances and additional fatty substances of 0.05 to 8.5 wt. % of the total weight of the agent.

12. The agent of claim 1, further comprising at least one amine oxide surfactant of formula (IV),

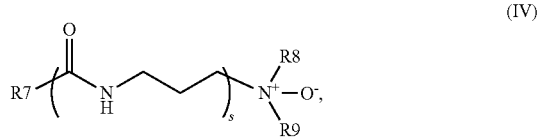

in which:
R7 denotes a saturated or unsaturated $C_6$-$C_{22}$ alkyl chain;
S denotes the number 0 or 1; and
R8 and R9 mutually independently denote hydrogen, a $C_1$-$C_4$ alkyl chain or a $C_2$-$C_4$ hydroxyalkyl chain.

13. The agent of claim 12, in which R8 and R9 of formula (IV) denote methyl, which is selected from Dimethyl Cocamine Oxide, Dimethyl Tallowamine Oxide, Dimethyl Decylamine Oxide, Dimethyl Lauramine Oxide, Dimethyl Myristamine Oxide, Dimethyl Palmitamine Oxide, Dimethyl Stearamine Oxide, Dimethyl Oleamine Oxide and Dimethyl Behenamine Oxide together with Dimethyl Cocamidopropylamine Oxide, Dimethyl Tallowamidopropylamine Oxide, Dimethyl Decylamidopropylamine Oxide, Dimethyl Lauramidopropylamine Oxide, Dimethyl Myristamidopropylamine Oxide, Dimethyl Palmitamidopropylamine Oxide and Dimethyl Stearamidopropylamine Oxide.

14. The agent of claim 12, in which the amine oxide surfactant of formula (IV) forms 0.01 to 5 wt. % of the total weight of the agent.

15. The agent of claim 1, in which the agent is to color human hair for improving hair care, for increasing color intensity and/or for improving color retention.

* * * * *